United States Patent
Hashmi et al.

(10) Patent No.: US 11,180,439 B2
(45) Date of Patent: Nov. 23, 2021

(54) METHOD OF REDUCING IMPURITIES IN A CATALYST FOR PRODUCING TEREPHTHALIC ACID

(71) Applicant: SABIC Global Technologies, B.V., Bergen op Zoom (NL)

(72) Inventors: Syed Azhar Hashmi, Riyadh (SA); Sankaran B. Nedumbamana, Bangalore (IN); Paresh Bhagvanbhai Rasadiya, Baroda (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 78 days.

(21) Appl. No.: 16/633,935

(22) PCT Filed: Aug. 9, 2018

(86) PCT No.: PCT/IB2018/056015
§ 371 (c)(1),
(2) Date: Jan. 24, 2020

(87) PCT Pub. No.: WO2019/030709
PCT Pub. Date: Feb. 14, 2019

(65) Prior Publication Data
US 2021/0087132 A1    Mar. 25, 2021

Related U.S. Application Data

(60) Provisional application No. 62/544,330, filed on Aug. 11, 2017.

(51) Int. Cl.
C07C 51/48    (2006.01)
B01J 38/64    (2006.01)
(Continued)

(52) U.S. Cl.
CPC ............... *C07C 51/48* (2013.01); *B01J 38/64* (2013.01); *C07C 51/487* (2013.01); *C07C 51/64* (2013.01); *C07C 63/26* (2013.01)

(58) Field of Classification Search
None
See application file for complete search history.

(56) References Cited

U.S. PATENT DOCUMENTS

| | | |
|---|---|---|
| 2,518,283 A | 8/1950 | Cassasa |
| 4,808,751 A | 2/1989 | Schroeder et al. |
| 7,282,151 B2 * | 10/2007 | Parker .................. B01J 31/4023 210/634 |

FOREIGN PATENT DOCUMENTS

| | | | |
|---|---|---|---|
| CN | 1285341 | * | 2/2001 |
| CN | 100355718 C | | 12/2007 |
| CN | 103028422 A | | 4/2013 |

OTHER PUBLICATIONS

Wikipedia page for Lye: https://en.wikipedia.org/wiki/Lye, downloaded on Jun. 16, 2021 (Year: 2021).*

(Continued)

Primary Examiner — Amy C Bonaparte
(74) Attorney, Agent, or Firm — Cantor Colburn LLP

(57) ABSTRACT

A method of reducing impurities in a catalyst for the production of purified terephthalic acid includes forming purified terephthalic acid by hydrogenating crude terephthalic acid with a catalyst in a reactor; separating the purified terephthalic acid from the catalyst and reactivating the catalyst by washing with a caustic solution; and flushing the catalyst contaminated with impurities with a non-caustic liquid at a flushing temperature of greater than or equal to 50° C.

20 Claims, 3 Drawing Sheets

(51) Int. Cl.
   *C07C 51/487*   (2006.01)
   *C07C 51/64*    (2006.01)
   *C07C 63/26*    (2006.01)

(56) References Cited

OTHER PUBLICATIONS

Kopnick ("Polyesters" Ullmann's Encyclopedia of Industrial Chemistry, published Jun. 15, 2000, downloaded from https://doi.org/10.1002/14356007.a21_227 on Jun. 17, 2021, p. 623-649) (Year: 2000).*
Merriam Webster (downloaded from https://www.merriam-webster.com/dictionary/caustic#:~:text=1%20%3A%20a%20caustic%20agent%3A%20such,alkali%20(such%20as%20sodium%20hydroxide on Jun. 22, 2021) (Year: 2021).*
International Search Report for International Application No. PCT/IB2018/056015; Application Filing Date Aug. 9, 2018; dated Nov. 8, 2018, 5 pages.
Written Opinion for International Application No. PCT/IB2018/056015; Application Filing Date Aug. 9, 2018; dated Nov. 8, 2018, 7 pages.

* cited by examiner

METHOD OF REDUCING IMPURITIES IN A CATALYST FOR PRODUCING TEREPHTHALIC ACID

CROSS REFERENCE TO RELATED APPLICATIONS

This application is a 371 of International Application No. PCT/IB2018/056015, filed Aug. 9, 2018, which is incorporated herein by reference in its entirety, and which claims priority to and the benefit of U.S. Provisional Application No. 62/544,330, filed Aug. 11, 2017.

BACKGROUND

Terephthalic acid is a commodity petrochemical of significant commercial importance. It is used as a key raw material for the production of various types of polymers. Polymer-grade or purified terephthalic acid is the starting material for polyethylene terephthalate, which is the principal polymer for polyester fibers, polyester films, and resins for bottles and similar containers. Purified terephthalic acid is produced commercially from relatively less pure, technical grade, or crude terephthalic acid. Crude terephthalic acid can be obtained by oxidation of the alkyl-aromatic compound p-xylene.

The oxidation of p-xylene can involve the use of an acetic acid solvent and a catalyst at high temperature. For example, catalysts can include bromine, cobalt, and manganese. Major impurities are formed during this process. For example, a crude terephthalic acid product can contain high levels of 4-carboxybenzaldehyde (4-CBA), p-toluic acid, benzoic acid, acetic acid, trimellitic acid, fluorenone, benzyl, and metal impurities such as iron, cobalt, manganese, or sodium. Maintaining the quality of purified terephthalic acid is important since impurities can lead to problems such as premature termination of polymerization, color related issues, excess metal contamination, etc. in the final product that will affect the overall quality and sales of polyethylene terephthalate (PET). The impurities formed during the production of crude terephthalic acid not only make the product unsuitable for further processing, but also discolor the product. For example, the impurity fluorenone is bright fluorescent yellow in color and can cause severe discoloration.

Accordingly, the crude terephthalic acid product must undergo a cumbersome purification process. For example, the catalyst activity decreases over time leading to off-spec product, necessitating reactivation of the catalyst by flushing with room temperature water to remove sodium. However, room temperature water does not remove sodium completely. Additionally, the porous nature of the catalyst leads to high levels of sodium contamination in the spent catalyst. Failure to flush the catalyst efficiently results in accumulation of high concentration of sodium in the catalyst bed, which causes catalyst poisoning and leaching of sodium metal into the purified terephthalic acid resulting in quality related issues in downstream PET products.

A hydrogenation catalyst regeneration method for purified terephthalic acid has been used in which the deactivated catalyst was washed with 0.1 to 5.0% caustic solution. However, there is no efficient flushing of the catalyst which means that sodium remains in the catalyst bed and leaches into the purified terephthalic acid product.

A hydrogenation catalyst regeneration method has been used in which the catalyst was washed, dried, and treated with 10% hydrochloric acid for 12 hours, followed by filtration of the catalyst and washing with water until the filtrate was free of chloride. However, this method suffers from disadvantages such as use of hydrochloric acid and the need for large amounts of water to remove all the chloride from the catalyst.

Thus, there is a need for a terephthalic acid purification method that can produce polymer-grade terephthalic acid without the cumbersome flushing procedure and product discoloration of conventional terephthalic acid purification methods.

SUMMARY

Disclosed, in various embodiments, are methods of purifying terephthalic acid.

A method of reducing impurities in a catalyst for the production of purified terephthalic acid, includes: forming purified terephthalic acid by hydrogenating crude terephthalic acid with a catalyst in a reactor; separating the purified terephthalic acid from the catalyst and reactivating the catalyst by washing with a caustic solution; and flushing the catalyst contaminated with impurities with a non-caustic liquid at a flushing temperature of greater than or equal to 50° C.

A method of reducing impurities in a catalyst for the production of purified terephthalic acid, comprising: forming purified terephthalic acid by hydrogenating crude terephthalic acid with a catalyst in a reactor; separating the purified terephthalic acid from catalyst and reactivating the catalyst by washing with a solution comprising sodium hydroxide; and flushing the catalyst contaminated with sodium hydroxide continuously with demineralized water at a flushing temperature of about 50° C. to about 250° C., preferably, about 75° C. to about 150° C., more preferably, about 90° C. to about 100° C.

A method of reducing impurities in a catalyst for the production of purified terephthalic acid, comprising: forming purified terephthalic acid by hydrogenating crude terephthalic acid with a catalyst in a reactor; separating the catalyst from the purified terephthalic acid and reactivating the catalyst by washing with a solution comprising sodium hydroxide; and flushing the catalyst contaminated with sodium hydroxide at a flushing temperature of about 50° C. to about 250° C., preferably, about 75° C. to about 150° C., more preferably, about 90° C. to about 100° C.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
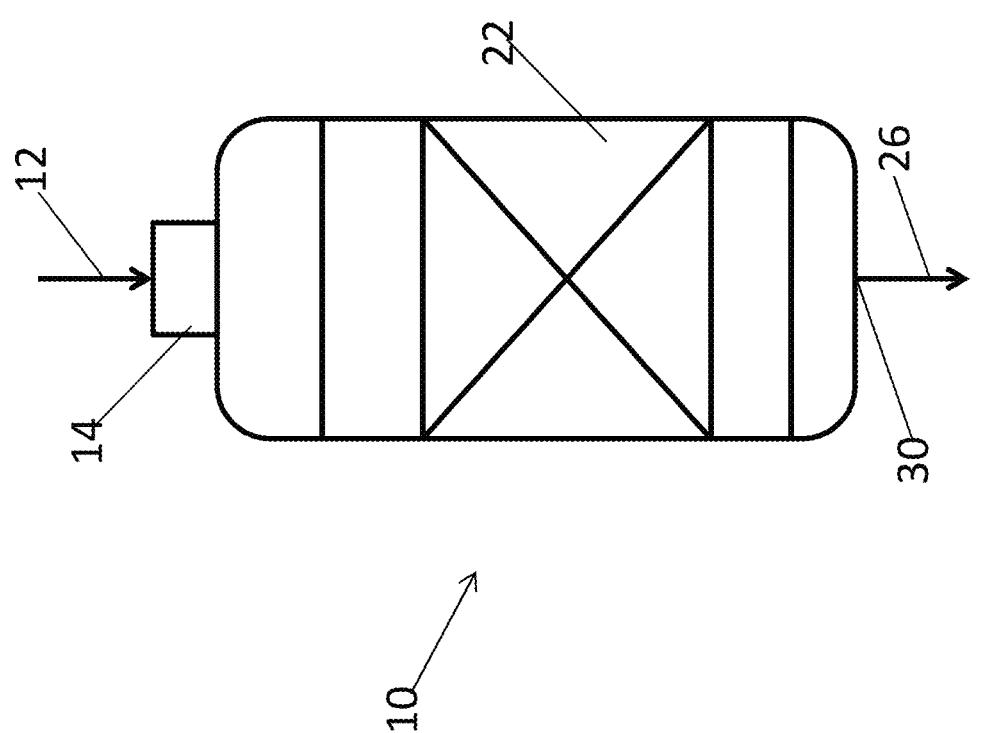
FIG. 1 is a simplified schematic diagram representing a method for purifying terephthalic acid in accordance with the present disclosure.

The method disclosed herein can produce polymer-grade terephthalic acid with a novel flushing process that can remove impurities from the contaminated purified terephthalic acid catalyst. If purified terephthalic acid catalyst activity decreases with time, it will lead to higher levels of the impurity 4-carboxybenzaldehyde (4-CBA) in the purified product, which leads to off-specification products. Catalyst deactivity requires reactivation of the catalyst by washing the catalyst with a solution, such as a 0.5% sodium hydroxide solution. The solution can impart impurities to the catalyst. After the solution wash, the catalyst can be flushed with water to remove the impurities, such as sodium. However, failure to wash the catalyst effectively results in accumulation of high concentrations of impurities in the catalyst bed, which causes poisoning and leaching of the metal into the purified terephthalic acid product. It is therefore recommended to keep the impurity levels as low as possible in the purified terephthalic acid product to reduce the possibility of producing off-specification purified terephthalic acid, which in turn can affect PET production and quality. Removing impurities from the contaminated catalyst can reduce catalyst poisoning and leaching of impurities into the purified terephthalic acid product. After flushing the catalyst with cold water, some impurities such as sodium still remain in the catalyst bed possibly due to the high porosity of the catalyst. In the method disclosed herein, it was surprisingly found that flushing the contaminated catalyst with a non-caustic liquid at a flushing temperature of greater than or equal to 50° C. can completely remove impurities from the catalyst bed.

Considering the downstream product, PET, the presence of higher amounts of sodium in PET can lead to haze in the polymer, which is undesirable. As shown in Table 1, haze values of PET increase with an increase in sodium levels in purified terephthalic acid. Table 1 therefore demonstrates that higher amounts of sodium in purified terephthalic acid can lead to haze in PET.

TABLE 1

| Haze value in PET | Sodium in purified terephthalic acid (ppm) |
|---|---|
| 4.4 | 5 |
| 6.67 | 10 |
| 7.07 | 15 |
| 8.68 | 20 |
| 9.02 | 25 |

A method of reducing impurities in a catalyst for the production of purified terephthalic acid can include forming purified terephthalic acid by hydrogenating crude terephthalic acid with a catalyst in a reactor. The purified terephthalic acid from the catalyst and reactivating the catalyst by washing with a caustic solution. The catalyst in the catalyst bed is contaminated with impurities after formation of the purified terephthalic acid. The impurities can be removed by flushing the catalyst in the catalyst bed with a non-caustic liquid at a temperature of greater than or equal to 50° C. The flushing temperature can be about 50° C. to about 250° C., for example, about 75° C. to about 150° C., for example, about 80° C. to about 125° C., for example, about 90° C. to about 100° C.

The non-caustic liquid can include any non-caustic liquid, including, but not limited to, water. The water can include distilled water, demineralized water, or a combination comprising at least one of the foregoing. The caustic solution can include a dilute alkaline solution. The dilute alkaline solution can include a hydroxide, a phase transfer catalyst, or a combination comprising at least one of the foregoing. The hydroxide can include sodium hydroxide, potassium hydroxide, ammonium hydroxide or a combination comprising at least one of the foregoing. The phase transfer catalyst can include a basic phase transfer catalyst. The basic phase transfer catalyst can include benzyltrimethyl ammonium hydroxide.

The catalyst contaminated with impurities can be flushed continuously. The catalyst contaminated with impurities can be flushed batch wise.

The impurities present in the catalyst can comprise a metal. The metal can include cobalt, manganese, sodium, iron, or a combination comprising at least one of the foregoing. The impurities present in the catalyst can include organic impurities such as 4-carboxybenzaldehyde, p-toluic acid, benzoic acid, acetic acid, trimellitic acid, fluorenone, benzyl, or a combination comprising at least one of the foregoing.

After flushing with the non-caustic liquid as described in the present method, impurities present in the catalyst can be reduced to an amount of less than or equal to 1000 parts per million (ppm). For example, sodium can be present in an amount of less than or equal to 1000 ppm. For example, after flushing with the non-caustic liquid as described in the present method, the catalyst can comprise at least one Group VIII noble metal-containing component on a support, e.g., an activated carbon support. Impurities, such as sodium, can be present in an amount of less than or equal to 1000 ppm.

The catalyst can be present in a reactor bed or a catalyst bed. In the continuous mode, the catalyst contaminated with caustic and other impurities can be flushed with less than or equal to 50 catalyst bed volumes of the non-caustic liquid, for example, less than or equal to 25 catalyst bed volumes of the non-caustic liquid, for example, less than or equal to 10 catalyst bed volumes of the non-caustic liquid.

In the batch wise mode, the catalyst contaminated with caustic and other impurities can be flushed with a non-caustic liquid with a ratio of water to catalyst equal to 50:1, for example, 25:1, for example, 15:1, for example, 10:1. The soaked time can be 30 minutes to 120 minutes, for example, 35 minutes to 100 minutes, for example, 40 minutes to 60 minutes. The soaked time refers to the time during which the catalyst is being flushed with the non-caustic liquid.

After flushing, the catalyst can be reused in the reactor for further formation of purified terephthalic acid. A polyethylene terephthalate polymer can be made from the purified terephthalic acid and reduced impurity catalyst formed from the method disclosed herein.

In an embodiment, a method of reducing impurities in a catalyst for the production of purified terephthalic acid can include forming purified terephthalic acid by hydrogenating crude terephthalic acid with a catalyst in a reactor and separating the purified terephthalic acid from the catalyst. The catalyst can be reactivated by washing with a solution comprising sodium hydroxide. The catalyst, which is now contaminated with sodium hydroxide, can then be flushed with water, for example, distilled or demineralized water, continuously or batch wise. The flushing temperature can be about 50° C. to about 250° C., for example, about 75° C. to about 150° C., for example, about 90° C. to about 100° C. With this method, the sodium content present in the catalyst can be reduced to less than or equal to 1000 ppm after flushing. The sodium content in the flushed water drained from the reactor can be less than or equal to 5 ppm. The conductivity of the flushed water can be less than or equal to 50 microSiemens per centimeter (0/cm). This conductivity value gives an indication of the low sodium content present in the flushed water.

Although flushing is described herein with respect to the catalyst bed or the reactor bed, it is to be understood that flushing can occur at any point within the reactor after the purified terephthalic acid has been formed. For example, the flushing can be applied downstream of the purified terephthalic acid reactor. For example, the flushing can occur in a rotary pressure filter (RPF), a rotary vacuum filter (RVF), product transfer lines, etc. Furthermore, it is noted that the method of flushing the catalyst used in the formation of purified terephthalic acid can be used in other purified terephthalic acid systems where sodium washing occurs.

The method disclosed herein for purifying terephthalic acid can include passing a feed stream through an entry point of a hydrogenation reactor. The feed stream can comprise crude terephthalic acid. The method can include passing the feed stream through a first non-catalytic bed to produce a filtered stream that exits the first non-catalytic bed. For example, the first non-catalytic bed can comprise porous ceramic structures, porous aluminum structures, or a combination comprising at least one of the foregoing. The first non-catalytic bed can occupy a percentage of a space located between the entry point and a catalytic bed. The filtered stream can pass through the catalytic bed after exiting the first non-catalytic bed. For example, a hydrogenation reaction can occur within the catalytic bed to produce a polymer-grade terephthalic acid stream that exits the catalytic bed. The polymer-grade terephthalic acid stream can then pass through a second non-catalytic bed to produce a product stream that exits the second non-catalytic bed. For example, a purity of the product stream can be greater than or equal to 99.95%. The product stream can then be further passed through a filter screen before being withdrawn from an exit point of the hydrogenation reactor. The second non-catalytic bed can comprise porous ceramic structures, porous aluminum structures, or a combination comprising at least one of the foregoing. The second non-catalytic bed can occupy a percentage of a space located between the catalytic bed and the exit point.

The method disclosed herein for purifying a catalyst for the production of purified terephthalic acid can include a feed stream. The source of the feed stream can be a product of a preliminary oxidation process. For example, the preliminary oxidation process can include the liquid oxidation of an alkyl-aromatic compound such as p-xylene, o-xylene, m-xylene, 1,2-bishydroxymethylbenzene, 2,6-dimethyl-naphthalene, or a combination comprising at least one of the foregoing. The preliminary oxidation process can include passing the alkyl-aromatic compound through an oxidation reactor and contacting the alkyl-aromatic compound with a catalyst comprising cobalt, manganese, chromium, copper, nickel, titanium, vanadium, iron, molybdenum, tin, cerium, zinc, lead, zirconium, cesium, silver, or a combination comprising at least one of the foregoing.

The feed stream can comprise terephthalic acid. For example, the feed stream can comprise crude terephthalic acid dissolved in demineralized water. The feed stream can comprise impurities. For example, the feed stream can comprise 4-CBA, p-toluic acid, benzoic acid, acetic acid, trimellitic acid, fluorenone, benzyl, metal impurities such as iron, cobalt, manganese, sodium, or a combination comprising at least one of the foregoing.

The method can include passing a feed stream through a hydrogenation reactor. For example, the reactor can be a down-flow, fixed-bed hydrogenation reactor. The feed stream can be passed through an entry point of the hydrogenation reactor. A temperature within the hydrogenation rector can be 100° C. to 1000° C., for example, a temperature within the hydrogenation reactor can be 150° C. to 500° C., 200° C. to 400° C., for example, 250° C. to 300° C. A pressure within the hydrogenation reactor can be 6000 kiloPascals to 10,000 kiloPascals. For example, a pressure within the hydrogenation reactor can be 7000 kiloPascals to 9000 kiloPascals.

The method disclosed herein can include passing a stream through a catalytic bed within a hydrogenation reactor. For example, the catalytic bed can be a fixed bed and can comprise a hydrogenation catalyst. For example, the catalytic bed can comprise any commercial hydrogenation catalyst. For example, the catalytic bed can comprise palladium, ruthenium, or a combination comprising at least one of the foregoing. The catalytic bed can comprise a catalyst support. For example, the catalyst support can comprise carbon, alumina, silica, titanium dioxide or a combination comprising at least one of the foregoing. The stream can contact the hydrogenation catalyst within the catalytic bed. For example, a hydrogenation reaction can occur producing a reaction stream that exits the catalytic bed. For example, the reaction stream can comprise purified terephthalic acid, i.e., polymer-grade terephthalic acid.

The method disclosed herein for purifying terephthalic acid can produce a commodity petrochemical of significant commercial importance. For example, the method disclosed herein can include withdrawing a product stream from an exit point of the hydrogenation reactor. For example, the product stream can comprise polymer-grade terephthalic acid. Terephthalic acid can be used as a key raw material for the production of various types of polymers. Polymer-grade or purified terephthalic acid is the starting material for polyethylene terephthalate, which is the principal polymer for polyester fibers, polyester films, and resins for bottles and similar containers. For example, the product stream of the method disclosed herein, comprising polymer-grade terephthalic acid, can be further polymerized with a diol to form polyester.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, the method disclosed herein can include passing a feed stream 12 through an entry point 14 of a hydrogenation reactor 10. The feed stream 12 can comprise crude terephthalic acid. The method can include passing the feed stream 12 through a catalytic bed 22. A hydrogenation reaction can occur within the catalytic bed 22 producing a polymer-grade terephthalic acid stream that exits the catalytic bed 22 as a product stream 26. The product stream 26 can then be withdrawn from the hydrogenation reactor 10 through an exit point 30.

The following examples are merely illustrative of the method disclosed herein and is not intended to limit the scope hereof.

EXAMPLES

Example 1

In Experiments 1 to 4, purified terephthalic acid samples containing large amounts of sodium metal contamination were analyzed. Table 2 lists the sodium content in ppm for each sample.

TABLE 2

Sodium content of samples

| Sample # | 1 | 2 | 3 | 4 | 5 | Average |
|---|---|---|---|---|---|---|
| Sodium Content (ppm) | 5127 | 4980 | 6471 | 4924 | 5860 | 5471 |

To reduce the level of sodium in the catalyst and for catalyst recycling, an efficient flushing procedure for sodium removal from contaminated purified terephthalic acid is needed. The novel method disclosed herein for removing impurities such as sodium from the purified terephthalic acid hydrogenation catalyst can reduce the level of impurities to an acceptable level. The flushing method was performed continuously and batch wise at various temperatures. In continuous mode, the flushing experiments were performed by using constant flow of demineralized water from a top to a bottom direction in a glass column packed with the catalyst. In batch wise mode, the catalyst was washed in a fixed bed catalyst basket.

In the continuous process, the contaminated catalyst was packed in a glass column and flushed demineralized water at room temperature and at 90° C. with seven liters of demineralized water for three days at a flow rate of 1.5 milliliters per minute (ml/min). The catalyst washing samples were collected at the bottom of the column and analyzed for sodium and chloride. The washed catalyst was analyzed for sodium content.

Example 1: Cold Water Flushing at Room Temperature in Continuous Mode

In this experiment, 25 grams (g) of the contaminated catalyst was packed in a glass column having a height of 50 centimeters (cm) and a diameter of 3 cm. Demineralized water was passed from the top of the column at a flow rate of 1.5 ml/min. The catalyst washing samples were collected at the bottom of the column and analyzed for sodium and chloride. The washed catalyst was analyzed for sodium content. The results of the catalyst sample are presented in Table 3.

Experiment 2: Hot Water Flushing at Room Temperature in Continuous Mode

In this experiment, 25 g of the contaminated catalyst was packed in a glass column having the same dimensions as in Experiment 1. The column was heated to 90° C. using a heating tape. Demineralized water at 90° C. was passed from the top of the column at a flow rate of 1.5 ml/min. The catalyst washing samples were collected at the bottom of the column and analyzed for sodium and chloride. The washed catalyst was analyzed for sodium content. The results of the analysis of the catalyst sample are presented in Table 3. Washing was done with various bed volumes (BV) of water.

TABLE 3

Continuous Mode Experiments

| Experiment # | Flushing Temperature | Sample Description | Sodium (ppm) |
|---|---|---|---|
| 1 | 23° C. | Sodium content in PTA catalyst after caustic wash before flushing | >5000 |
| | | Sodium content in PTA catalyst after washing with 10 BV of water | 4100 |
| | | Sodium content in PTA catalyst after washing with 165 BV of water | 862 |
| 2 | 90° C. | Sodium content in PTA catalyst before flushing | >5000 |
| | | Sodium content in PTA catalyst after washing with 10 BV of water | 943 |

Figure 2:
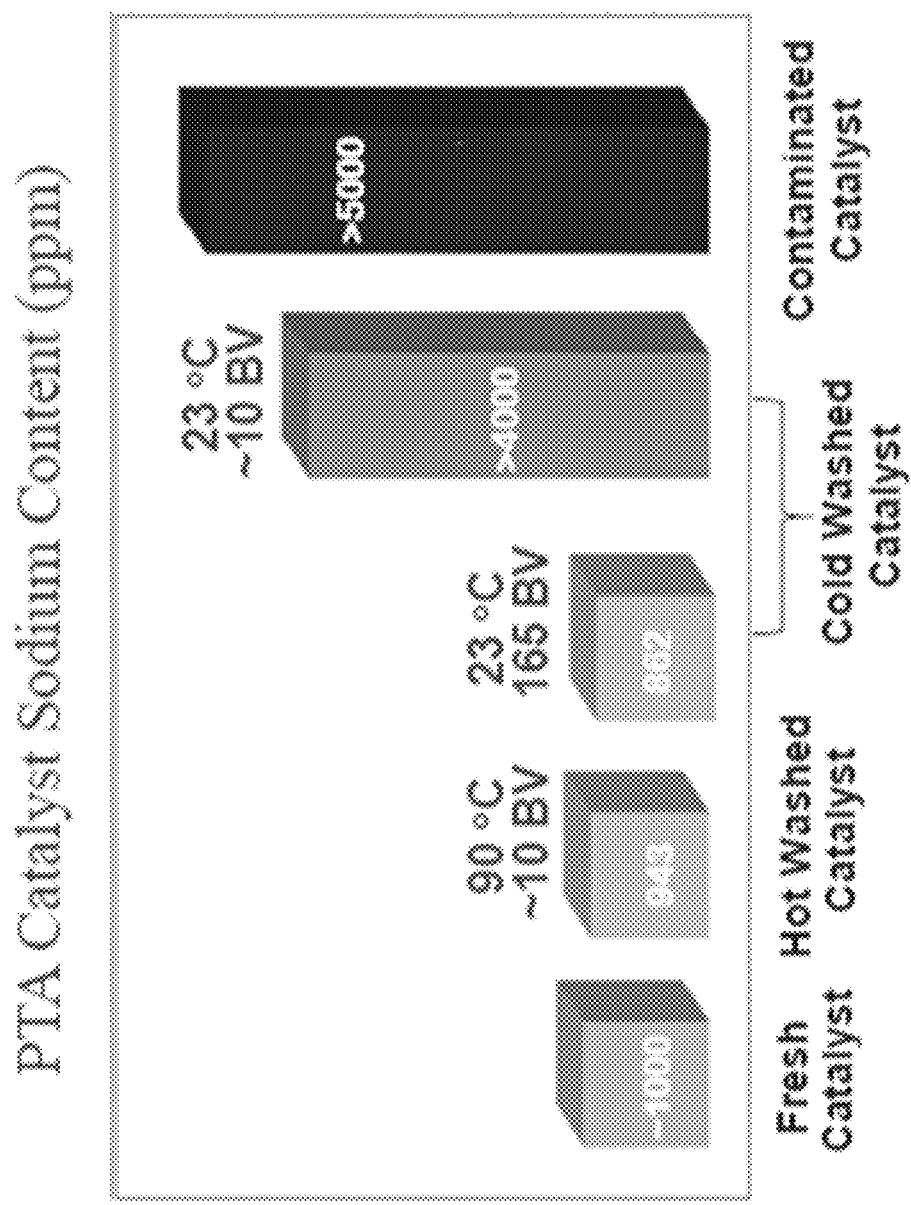
FIG. 2 is a graphical representation of the continuous mode of experiments.

The results in Table 3 demonstrate that the catalyst flushing experiments using room temperature water (23° C.) by continuous mode of operation partially removes sodium from the catalyst. However, it is not effective to reduce the sodium content in the catalyst. The sodium content was lowered to 4100 ppm after washing with 10 BV of water. It required very high bed volumes of water (165 BV) and longer washing times to reduce sodium content in the catalyst to less than 1000 ppm. It was surprisingly discovered that flushing of the purified terephthalic acid catalyst using higher temperature water (90° C.) by the continuous mode of operation is an effective method to reduce sodium content in the catalyst. As shown in Table 3, the sodium content was lowered to 943 ppm after washing with 10 BV of water. The results of Table 3 are represented graphically in FIG. 2.

Experiment 3: Cold Water Flushing at Room Temperature in Batch Wise Mode

In this experiment, 25 g of the contaminated catalyst was packed in a catalyst basket and continuously stirred using demineralized water at room temperature for 45 minutes. The washing samples were collected and analyzed for sodium and chloride. The washed catalyst was analyzed for sodium content. The results of the analysis and catalyst samples are presented in Table 4.

Experiment 4: Hot Water Flushing at 90° C. in Batch Wise Mode

In this experiment, 25 g of the contaminated catalyst was packed in a catalyst basket and continuously stirred using demineralized water at 90° C. for 45 minutes. The washing samples were collected and analyzed for sodium and chloride. The washed catalyst was analyzed for sodium content. The results of the analysis and catalyst samples are presented in Table 4.

TABLE 4

Batch Wise Experiments

| Experiment # | Flushing Temperature | Sample Description | Sodium (ppm) |
|---|---|---|---|
| 3 | 23° C. | Sodium content in PTA catalyst before flushing | >5000 |
| | | Sodium content in PTA catalyst after washing with 0.4 liter of water | 4200 |

TABLE 4-continued

Batch Wise Experiments

| Experiment # | Flushing Temperature | Sample Description | Sodium (ppm) |
|---|---|---|---|
| | | Sodium content in PTA catalyst after washing with 7.0 liter of water | 978 |
| 4 | 90° C. | Sodium content in PTA catalyst before flushing | >5000 |
| | | Sodium content in PTA catalyst after washing with 0.4 liter of water | 940 |

Figure 3:
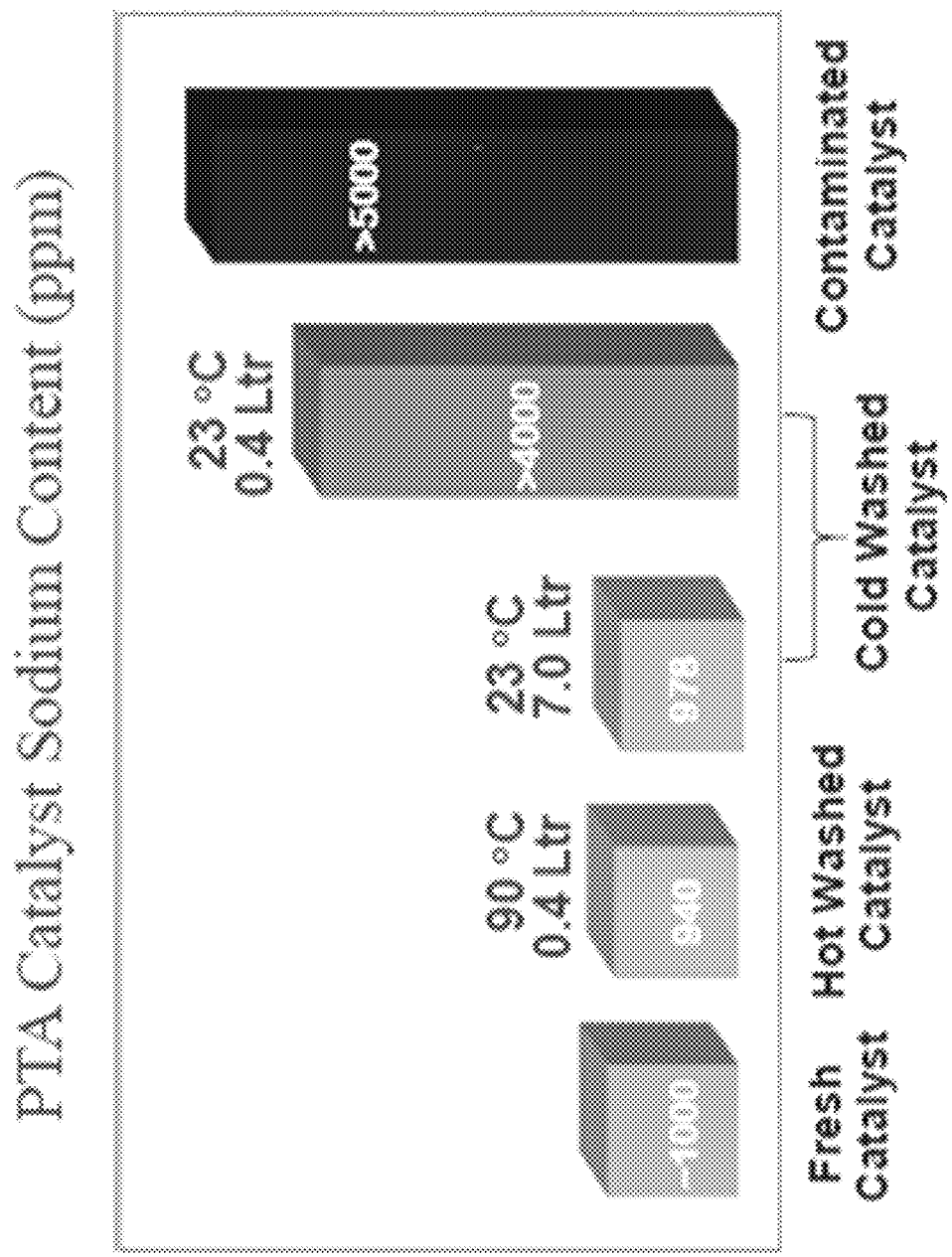
FIG. 3 is a graphical representation of the batch wise mode of experiments.

The results in Table 4 demonstrate that the catalyst flushing experiments using room temperature water (23° C.) by batch wise mode of operation partially removes sodium from the catalyst. However, it is not effective to reduce the sodium content in the catalyst. The sodium content was lowered to 4200 ppm after washing with 10 BV of water. It required very high bed volumes of water (165 BV) and longer washing times to reduce sodium content in the catalyst to less than 1000 ppm. It was surprisingly discovered that flushing of the purified terephthalic acid catalyst using higher temperature water (90° C.) by the batch wise mode of operation is an effective method to reduce sodium content in the catalyst. As shown in Table 4, the sodium content was lowered to 940 ppm after washing with 10 BV of water. The results of Table 4 are represented graphically in FIG. 3.

The flushed water from Experiments 1 to 4 were analyzed for its pH, conductivity, turbidity, and delta Y. The pH was measured using a portable OHAUS waterproof pen meter. The pH was measured according to ASTM D-123. Turbidity measurements were carried out using a HACH 2100Q Portable Turbidimeter. Turbidity was measured according to ASTM D7726. Conductivity measurements were performed using a Fischer Scientific Model: AR 50 Accumet dual channel pH/Ion/Conductivity meter. Conductivity was measured according to ASMT D-1126. Analysis for the determination of color values (delta Y) were carried out using a BYK Gardner, Tristimulus color Difference Meter (Colorguard System 2000/5 Colorimeter) where the tristimulus color difference meter determines the color of the sample in three photocells which are preceded by a red, green and blue filter respectively.

Based on the analysis, a correlation was developed for sodium in the flushed water and the various monitoring parameters at various temperatures. The data is presented in Table 5. Such analysis makes the measurement of sodium in the purified terephthalic acid catalyst rapid and non-cumbersome allowing for an easy method for monitoring sodium levels in flushed water samples in purified terephthalic acid facilities.

TABLE 5

Analysis of Flushed Water

| DM Water + Na | Temp. 20° C. | | | | Temp. 30° C. | | | |
|---|---|---|---|---|---|---|---|---|
| | pH | Conductivity (µS/cm) | Turbidity (NTU) | Delta Y | pH | Conductivity (µS/cm) | Turbidity (NTU) | Delta Y |
| Blank Water | 6.45 | 1.22 | 0.1 | 0 | 6.38 | 1.74 | 0.2 | 0 |
| 5 ppm | 10.3 | 38.9 | 0.3 | 0 | 10.1 | 50.5 | 0.4 | 0 |
| 10 ppm | 10.8 | 92.4 | 0.3 | 0 | 10.5 | 108 | 0.4 | 0 |
| 15 ppm | 11 | 145 | 0.3 | 0 | 10.8 | 161 | 0.4 | 0 |
| 20 ppm | 11.2 | 194 | 0.3 | 0 | 10.9 | 222 | 0.4 | 0 |
| 25 ppm | 11.3 | 245 | 0.3 | 0 | 11 | 294 | 0.4 | 0 |
| 30 ppm | 11.3 | 306 | 0.3 | 0 | 11.1 | 356 | 0.4 | 0 |
| 35 ppm | 11.4 | 355 | 0.3 | 0 | 11.1 | 403 | 0.4 | 0 |
| 40 ppm | 11.5 | 410 | 0.3 | 0 | 11.2 | 465 | 0.4 | 0 |
| 45 ppm | 11.5 | 462 | 0.3 | 0 | 11.3 | 527 | 0.4 | 0 |
| 50 ppm | 11.6 | 521 | 0.3 | 0 | 11.3 | 586 | 0.4 | 0 |

| DM Water + Na | Temp. 50° C. | | | | Temp. 70° C. | | | |
|---|---|---|---|---|---|---|---|---|
| | pH | Conductivity (µS/cm) | Turbidity (NTU) | Delta Y | pH | Conductivity (µS/cm) | Turbidity (NTU) | Delta Y |
| Blank Water | 6.31 | 2.85 | 0.3 | 0 | 6.21 | 5.62 | 0.3 | 0 |
| 5 ppm | 9.43 | 55.8 | 0.5 | 0 | 8.65 | 56.7 | 0.6 | 0 |
| 10 ppm | 9.87 | 129 | 0.5 | 0 | 9.13 | 138 | 0.6 | 0 |
| 15 ppm | 10.18 | 207 | 0.5 | 0 | 9.39 | 232 | 0.6 | 0 |
| 20 ppm | 10.35 | 296 | 0.5 | 0 | 9.54 | 309 | 0.6 | 0 |
| 25 ppm | 10.49 | 374 | 0.5 | 0 | 9.84 | 453 | 0.6 | 0 |
| 30 ppm | 10.54 | 462 | 0.5 | 0 | 9.85 | 531 | 0.6 | 0 |
| 35 ppm | 10.59 | 550 | 0.5 | 0 | 9.92 | 641 | 0.6 | 0 |
| 40 ppm | 10.67 | 634 | 0.5 | 0 | 10.03 | 740 | 0.6 | 0 |
| 45 ppm | 10.72 | 710 | 0.5 | 0 | 10.1 | 835 | 0.6 | 0 |
| 50 ppm | 10.78 | 792 | 0.5 | 0 | 10.3 | 926 | 0.6 | 0 |

| DM Water + Na | Temp. 90° C. | | | |
|---|---|---|---|---|
| | pH | Conductivity (µS/cm) | Turbidity (NTU) | Delta Y |
| Blank Water | 6.11 | 6.5 | 0.3 | 0 |
| 5 ppm | 8.45 | 59.8 | 0.8 | 0 |
| 10 ppm | 8.91 | 158 | 0.8 | 0 |
| 15 ppm | 9.24 | 267 | 0.8 | 0 |

TABLE 5-continued

| Analysis of Flushed Water | | | | |
|---|---|---|---|---|
| 20 ppm | 9.36 | 356 | 0.8 | 0 |
| 25 ppm | 9.08 | 509 | 0.8 | 0 |
| 30 ppm | 9.25 | 598 | 0.8 | 0 |
| 35 ppm | 9.46 | 713 | 0.8 | 0 |
| 40 ppm | 9.7 | 837 | 0.8 | 0 |
| 45 ppm | 9.81 | 923 | 0.8 | 0 |
| 50 ppm | 9.85 | 1040 | 0.8 | 0 |

Example 2

In this example, hot water flushing at 90° C. using the method disclosed herein was used for complete sodium removal from the contaminated purified terephthalic acid catalyst. In this example, 100 g of purified terephthalic acid catalyst was weighed and transferred into a cylindrical column having a length of 100 cm. Demineralized water heated to 80° C. is flushed through the column for 60 minutes. After completely eluting the solvent, the solid catalyst was removed from the column and dried. The catalyst sample and the eluted solutions were analyzed for sodium content by inductively coupled plasma optical emission spectroscopy (ICP-OES). Results are demonstrated in Tables 6 and 7.

TABLE 6

| Sample # | Sodium Content (ppm) |
|---|---|
| 1 | 1981 |
| 2 | 916 |
| 3 | 522 |
| 4 | 462 |
| 5 | 237 |
| 6 | 115 |
| 7 | <5 |

TABLE 7

| Sample Description | Sodium (ppm) |
|---|---|
| Catalyst sample before caustic washing | <1000 |
| Catalyst sample after caustic washing | ~5000 |
| Catalyst sample after hot DM water flushing | <1000 |

Example 3

In this example, it was demonstrated that flushing the catalyst with low temperature water or ambient water is not efficient for complete removal of sodium from the catalyst bed. This example was performed identically to that described in Example 2 except that it was performed at low temperature. 100 g of purified terephthalic acid hydrogenation catalyst was weighed and transferred into a cylindrical column having a length of 100 cm. Demineralized water heated to 25° C. was flushed through the column for 60 minutes. After completely eluting the solvent, the solid catalyst was removed from the column and dried. The catalyst sample and the eluted solutions were analyzed for sodium content by ICP-OES and results are shown in Tables 8 and 9. This example shows that flushing the catalyst with low temperature water is not efficient for complete removal of sodium from the catalyst bed.

TABLE 8

| Sample # | Sodium Content (ppm) |
|---|---|
| 1 | 516.6 |
| 2 | 262 |
| 3 | 135 |
| 4 | 60 |
| 5 | 28 |
| 6 | 8.0 |
| 7 | 6.0 |

TABLE 9

| Sample Description | Sodium (ppm) |
|---|---|
| Catalyst sample before caustic washing | <1000 |
| Catalyst sample after caustic washing | ~5000 |
| Catalyst sample after cold DM water flushing | >4000 |

The methods disclosed herein include(s) at least the following aspects:

Aspect 1: A method of reducing impurities in a catalyst for the production of purified terephthalic acid, comprising: forming purified terephthalic acid by hydrogenating crude terephthalic acid with a catalyst in a reactor; separating the purified terephthalic acid from the catalyst and reactivating the catalyst by washing with a caustic solution; and flushing the catalyst contaminated with impurities with a non-caustic liquid at a flushing temperature of greater than or equal to 50° C.

Aspect 2: The method of Aspect 1, wherein the flushing temperature is about 50° C. to about 250° C., preferably, about 75° C. to about 150° C., more preferably, about 90° C. to about 100° C.

Aspect 3: The method of Aspect 1 or Aspect 2, wherein non-caustic liquid comprises water, preferably, wherein the non-caustic liquid comprises distilled, demineralized water, or a combination comprising at least one of the foregoing.

Aspect 4: The method of any of the preceding aspects, wherein the flushing of the catalyst contaminate with impurities occurs continuously or wherein flushing of the catalyst contaminated with impurities occurs batch wise.

Aspect 5: The method of any of the preceding aspects, wherein the caustic solution comprises a hydroxide of sodium, potassium, or ammonium, a basic phase transfer catalyst, preferably, benzyltrimethyl ammonium hydroxide, or a combination comprising at least one of the foregoing.

Aspect 6: The method of any of the preceding aspects, wherein the impurities present in the catalyst comprise sodium, cobalt, manganese, or a combination comprising at least one of the foregoing.

Aspect 7: The method of any of the preceding aspects, wherein the catalyst after flushing comprises at least one Group VIII noble metal-containing component on an activated carbon support comprising sodium in an amount of less than or equal to 1000 parts per million.

Aspect 8: The method of any of the preceding aspects, wherein the impurities present in the catalyst are reduced to an amount of less than 1000 parts per million after flushing with the non-caustic liquid.

Aspect 9: The method of any of the preceding aspects, wherein sodium impurities present in the catalyst are reduced to an amount of less than 1000 parts per million after flushing with the non-caustic liquid.

Aspect 10: The method of any of the preceding aspects, wherein the catalyst contaminated with impurities is present in a reactor bed.

Aspect 11: The method of Aspect 10, wherein the catalyst contaminated with caustic and other impurities is flushed with less than or equal to 50 catalyst bed volumes of the non-caustic liquid in the continuous mode, preferably, less than or equal to 25 catalyst bed volumes of the non-caustic liquid, more preferably, less than or equal to 10 catalyst bed volumes of the non-caustic liquid.

Aspect 12: The method of Aspect 10, wherein the catalyst contaminated with caustic and other impurities is flushed with non-caustic liquid in the batch mode with a ratio of water to catalyst equal to 50:1, preferably, 25;1, more preferably 15:1, even more preferably, 10;1 with a soaked time of 40 minutes to 60 minutes.

Aspect 13: The method of Aspect 10, wherein the catalyst is reused in the reactor for further formation of purified terephthalic acid.

Aspect 14: A polyethylene terephthalate polymer made from the purified terephthalic acid and reduced impurity catalyst of any of the preceding aspects.

Aspect 15: A method of reducing impurities in a catalyst for the production of purified terephthalic acid, comprising: forming purified terephthalic acid by hydrogenating crude terephthalic acid with a catalyst in a reactor; separating the purified terephthalic acid from catalyst and reactivating the catalyst by washing with a solution comprising sodium hydroxide; and flushing the catalyst contaminated with sodium hydroxide continuously with demineralized water at a flushing temperature of about 50° C. to about 250° C., preferably, about 75° C. to about 150° C., more preferably, about 90° C. to about 100° C.

Aspect 16: The method of Aspect 15, wherein the sodium content in the catalyst after flushing is less than or equal to 1000 parts per million.

Aspect 17: The method of Aspect 15 or Aspect 16, wherein the sodium content in the flushed water drain from reactor is less than or equal to 5 parts per million and the conductivity of the flushed water is less than or equal to 50 microSiemens per centimeter.

Aspect 18: A method of reducing impurities in a catalyst for the production of purified terephthalic acid, comprising: forming purified terephthalic acid by hydrogenating crude terephthalic acid with a catalyst in a reactor; separating the catalyst from the purified terephthalic acid and reactivating the catalyst by washing with a solution comprising sodium hydroxide; and flushing the catalyst contaminated with sodium hydroxide at a flushing temperature of about 50° C. to about 250° C., preferably, about 75° C. to about 150° C., more preferably, about 90° C. to about 100° C.

Aspect 19: The method of any of the preceding aspects, wherein the flushing is applied downstream of the purified terephthalic acid reactor.

Aspect 20: The method of Aspect 19, wherein the flushing occurs in a rotary pressure filter, a rotary vacuum filter, or product transfer lines.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

Unless otherwise specified herein, any reference to standards, regulations, testing methods and the like, such as ASTM D1003, ASTM D4935, ASTM 1746, FCC part 18, CISPR11, and CISPR 19 refer to the standard, regulation, guidance or method that is in force at the time of filing of the present application.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of reducing impurities in a catalyst for the production of purified terephthalic acid, comprising:
   forming purified terephthalic acid by hydrogenating crude terephthalic acid with a catalyst comprising at least one Group VIII noble metal-containing component on a support in a reactor;
   separating the purified terephthalic acid from the catalyst and reactivating the catalyst by washing with an alkaline solution comprising a hydroxide of sodium, potassium, or ammonium, a basic phase transfer catalyst, or a combination comprising at least one of the foregoing; and
   flushing the catalyst with a non-alkaline liquid at a flushing temperature of about 50° C. to about 150° C. to remove impurities from the catalyst imparted by the alkaline solution.

2. The method of claim 1, wherein the flushing temperature is about 75° C. to about 150° C.

3. The method of claim 1, wherein the non-alkaline liquid comprises demineralized water.

4. The method of claim 1, wherein the flushing of the catalyst contaminated with impurities comprises continuously flushing the catalyst contaminated with impurities or wherein flushing of the catalyst comprises batch wise flushing of the catalyst contaminated with impurities.

5. The method of claim 1, wherein the alkaline solution comprises a hydroxide of sodium.

6. The method of claim 1, wherein the impurities present in the catalyst comprise sodium.

7. The method of claim 6, wherein the washing contaminates the catalyst with sodium, and wherein the flushing reduces sodium present in the catalyst to an amount of less than or equal to 1000 parts per million.

8. The method of claim 1, wherein the washing contaminates the catalyst with impurities, and wherein the flushing reduces impurities present in the catalyst to an amount of less than 1000 parts per million.

9. The method of claim 1, wherein the catalyst is present in a reactor bed of the reactor, and wherein the separating, washing, and flushing take place in the reactor.

10. The method of claim 9, comprising continuously flushing the catalyst contaminated with impurities with less than or equal to 50 catalyst bed volumes of the non-alkaline liquid.

11. The method of claim 9, comprising batch wise flushing the catalyst contaminated with impurities with the non-alkaline liquid, wherein the non-alkaline liquid comprises water, and with a ratio of water to catalyst equal to 50:1 with a soaked time of 40 minutes to 60 minutes.

12. The method of claim 9, further comprising reusing the catalyst in the reactor for further formation of purified terephthalic acid.

13. A method of making a polyethylene terephthalate polymer, the method comprising:
    reducing impurities in a catalyst according to the method of claim 1; and
    polymerizing the purified terephthalic acid separated from the catalyst with ethylene glycol to make the polyethylene terephthalate polymer.

14. A method of reducing impurities in a catalyst for the production of purified terephthalic acid, comprising:
    forming purified terephthalic acid by hydrogenating crude terephthalic acid with a catalyst comprising at least one Group VIII noble metal-containing component on a support in a reactor;
    separating the purified terephthalic acid from the catalyst and reactivating the catalyst by washing with a solution comprising sodium hydroxide; and
    flushing the catalyst continuously with demineralized water at a flushing temperature of about 50° C. to about 150° C. to remove sodium hydroxide from the catalyst imparted by the solution comprising sodium hydroxide.

15. The method of claim 14, wherein the washing contaminates the catalyst with sodium, and wherein the flushing reduces a sodium content in the catalyst to an amount of less than or equal to 1000 parts per million.

16. The method of claim 14, wherein the separating, washing, and flushing take place in the reactor, and wherein the sodium content in the flushed water drained from the reactor is less than or equal to 5 parts per million and the conductivity of the flushed water is less than or equal to 50 microSiemens per centimeter.

17. A method of reducing impurities in a catalyst for the production of purified terephthalic acid, comprising:
    forming purified terephthalic acid by hydrogenating crude terephthalic acid with a catalyst comprising at least one Group VIII noble metal-containing component on a support in a reactor;
    separating the catalyst from the purified terephthalic acid and reactivating the catalyst by washing with a solution comprising sodium hydroxide; and
    flushing the catalyst with water at a flushing temperature of about 50° C. to about 150° C. to remove sodium hydroxide from the catalyst imparted by the solution comprising sodium hydroxide.

18. The method of claim 17, comprising flushing the catalyst downstream of the purified terephthalic acid reactor.

19. The method of claim 18, comprising flushing the catalyst in a rotary pressure filter, a rotary vacuum filter, or product transfer lines.

20. The method of claim 1, wherein the flushing temperature is about 80° C. to about 125° C.

* * * * *